(12) United States Patent
Gibbons, Jr. et al.

(10) Patent No.: US 10,893,929 B2
(45) Date of Patent: Jan. 19, 2021

(54) VASCULAR GRAFT WITH COMPARTMENTS FOR COMPLIANCE MATCHING

(71) Applicant: Cook Medical Technologies LLC, Bloomington, IN (US)

(72) Inventors: William S. Gibbons, Jr., Bloomington, IN (US); Kenneth A. Haselby, Battle Ground, IN (US); Jarin A. Kratzberg, Lafayette, IN (US); Keith R. Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 426 days.

(21) Appl. No.: 15/867,477

(22) Filed: Jan. 10, 2018

(65) Prior Publication Data
US 2019/0209283 A1    Jul. 11, 2019

(51) Int. Cl.
*A61F 2/06* (2013.01)
*A61F 2/07* (2013.01)
*A61M 1/36* (2006.01)

(52) U.S. Cl.
CPC ............... *A61F 2/064* (2013.01); *A61F 2/06* (2013.01); *A61F 2/07* (2013.01); *A61M 1/3655* (2013.01);
(Continued)

(58) Field of Classification Search
CPC .... A61F 2/064; A61F 2/06; A61F 2/07; A61F 2250/0018; A61F 2002/068;
(Continued)

(56) References Cited

U.S. PATENT DOCUMENTS 6,312,462 B1 * 11/2001 McDermott ............. A61F 2/07
623/1.25
6,395,019 B2    5/2002 Chobotov
(Continued)

FOREIGN PATENT DOCUMENTS

WO    WO 99/39662 A1    8/1999
WO    WO 01/66038 A2    9/2001
(Continued)

OTHER PUBLICATIONS

European Search Report for EP Application No. 19275002.4, dated May 23, 2019, 7 pages.
(Continued)

*Primary Examiner* — Ophelia A Hawthorne
*Assistant Examiner* — Alessandro R Del Priore
(74) *Attorney, Agent, or Firm* — Brinks Gilson & Lione

(57) ABSTRACT

A graft having a tubular body having a first end configured for attachment to a first vessel having a first compliance and second end configured for attachment to a second vessel having a second compliance different from the first compliance, and having a plurality of compressible chambers in the wall of the tubular body in which the chamber adjacent the first end of the tubular body is less compressible than the chamber adjacent the second end of the tubular body such that first end of the tubular body substantially matches the first compliance and the second end of the tubular body substantially matches the second compliance.

18 Claims, 2 Drawing Sheets

(52) U.S. Cl.
CPC . *A61F 2002/068* (2013.01); *A61F 2250/0003* (2013.01); *A61F 2250/0018* (2013.01)

(58) Field of Classification Search
CPC ............ A61F 2250/0003; A61F 2/958; A61M 1/3655; A61M 25/104; F15D 1/065
See application file for complete search history.

(56) References Cited

U.S. PATENT DOCUMENTS

| | | |
|---|---|---|
| 7,682,673 B2 | 3/2010 | Houston et al. |
| 8,454,674 B2 | 6/2013 | Houston et al. |
| 8,454,675 B2 | 6/2013 | Houston et al. |
| 2002/0055709 A1* | 5/2002 | Weinberger ............ A61F 2/958 604/96.01 |
| 2003/0028211 A1* | 2/2003 | Crocker .................... A61F 2/86 606/192 |
| 2006/0047334 A1 | 3/2006 | Houston |
| 2007/0021707 A1 | 1/2007 | Caro et al. |
| 2010/0010518 A1 | 1/2010 | Stopek |
| 2014/0039537 A1* | 2/2014 | Carrison .......... A61B 17/12027 606/194 |
| 2017/0007754 A1 | 1/2017 | Babbs et al. |
| 2017/0008854 A1 | 1/2017 | Babbs et al. |

FOREIGN PATENT DOCUMENTS

| | | |
|---|---|---|
| WO | WO 2004/060214 A1 | 7/2004 |
| WO | WO 2011/133019 A2 | 10/2011 |

OTHER PUBLICATIONS

European Search Report for EP Application No. 19275004.0, dated May 23, 2019, 8 pages.

* cited by examiner

VASCULAR GRAFT WITH COMPARTMENTS FOR COMPLIANCE MATCHING

BACKGROUND

Technical Field

This invention relates generally to medical devices and particularly to an endoluminal or subcutaneous graft for improving vascular compliance of a vessel.

Background

A primary physiological function of the aorta and its major branches is to convert the highly pulsative output of the left ventricle to a more nearly uniform and steady flow in the arterioles and capillaries, with minimum loss of energy. This requires that the peripheral vascular input impedance (which is a complex function of arterial resistance, fluid inertance, and arterial compliance) be matched to the output impedance of the heart.

Compliance is the ability of a vessel to distend and increase volume with increasing transmural pressure or to resist recoil towards its original dimensions on application of a distending or compressing force. Compliance can be defined as the fractional change in volume per change in pressure. In compliance, an increase in volume occurs in a vessel when the pressure in that vessel is increased. The tendency of the arteries and veins to stretch in response to pressure has a large effect on perfusion and blood pressure. Blood vessels with a higher compliance deform easier than lower compliance blood vessels under the same pressure and volume conditions. Veins have a much higher compliance than arteries (largely due to their thinner walls).

When a vessel loses compliance, it loses elasticity and typically becomes stiffer. Vessels, such as the aorta, can lose compliance due to age, congestive heart failure, atherosclerosis, etc. As the aorta stiffens and loses compliance, the heart struggles to pump blood and must work harder to eject the same volume of blood from the left ventricle into the aorta with each heartbeat. For example, a young person has a typical compliance of 6% dilation of the aorta with each heartbeat, whereas an older person with some arterial disease has a typical compliance of only 3%. If the heart is incapable of working harder because of underlying diseases, then less blood will be ejected into the aorta with each heartbeat.

A prostheses may be inserted into a body lumen such as an anatomical vessel or duct for various purposes. Prostheses may maintain or restore patency in a formerly blocked or constricted passageway or they may be used for different procedures, such as to facilitate dialysis.

Existing vascular grafts, including stent-grafts, covered stents, arterial bypass grafts, and arterio-venous grafts may be prone to stenosis or neointimal hyperplasia at the ends of the grafts, especially where the venous end of arterio-venous grafts are sutured to the vein. This occurrence has been attributed to a mismatch in the compliance of the graft compared to the vein. The graft may be substantially less compliant than the vein, which may lead to mechanical stresses on the vein and hemodynamic changes.

Compliance mismatch between implanted devices and the adjacent vessel is believed to be one of the mechanisms leading to stenosis at the anastomoses of vascular grafts, particularly on the venous anastomosis of arterio-venous grafts, where the compliance mismatch is greatest. In one example, stenosis at the venous anastomosis is the primary failure mode for arterio-venous grafts used for hemodialysis vascular access.

It is therefore desirable to have a device configured such that the graft compliance matches that of an adjacent blood vessel so that stress on the vessel is reduced. As a result, stenosis may be reduced and the graft may have improved function and durability.

SUMMARY OF INVENTION

A graft having a tubular body having a first end configured for attachment to a first vessel having a first compliance and second end configured for attachment to a second vessel having a second compliance different from the first compliance, and having a plurality of compressible chambers in the wall of the tubular body in which the chamber adjacent the first end of the tubular body is less compressible than the chamber adjacent the second end of the tubular body such that the first end of the tubular body substantially matches the first compliance and the second end of the tubular body substantially matches the second compliance.

The first vessel may be an artery and the second vessel a vein, and the first end has a compliance configured to substantially match the compliance of the artery and the second end has a compliance configured to substantially match the compliance of the vein. There may be a compliance gradient from the first end to the second end, wherein the compliance of the graft increases from the first end to the second end.

DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

DETAILED DESCRIPTION OF THE PREFERRED EMBODIMENTS

As used here, the term "proximal" when referring to a delivery device refers to a direction that is farthest away from the operator using a delivery device, while the term "distal" refers to a direction that is generally closest to the operator using the delivery device. The proximal and distal ends of a delivery device can also be referred to as the introduction end of the delivery device and the operator end of the delivery device, respectively. The operator end of the delivery device is that portion of the device that is intended to remain outside of a patient during a procedure. When referring to the prosthesis itself relative to the delivery device, the proximal end of the prosthesis is that part of the prosthesis nearest the delivery end of the delivery device and the distal end of the prosthesis is that end that is closest to the operator end of the delivery device. When referring to the prosthesis relative to placement in the human body, the ends of the various devices and parts of devices may be referred to as the inflow end (that end that receives fluid first), and the outflow end (that end from which the fluid exits). When used herein, the term "compliance" is referred to as the fractional change in volume per unit change in pressure.

The present disclosure relates to the subject matter of U.S. application Ser. No. 14/791,712, filed Jul. 6, 2015, published as US 2017/0007754 A1, and entitled "Endovascular Compliance Assembly," which is incorporated by reference herein in its entirety.

Grafts of the present invention may be placed endoluminally. A graft may also be placed subcutaneously or surgically. With dialysis access grafts, grafts in the patient forearm or upper arm are placed surgically by suturing one end of the graft to an end or side of an artery, suturing the other end of the graft to an end or side of a vein, while the remainder of the graft is placed subcutaneously in the forearm or upper arm (i.e. the graft is placed subcutaneously and not within the lumen of another vessel).

Figure 1:
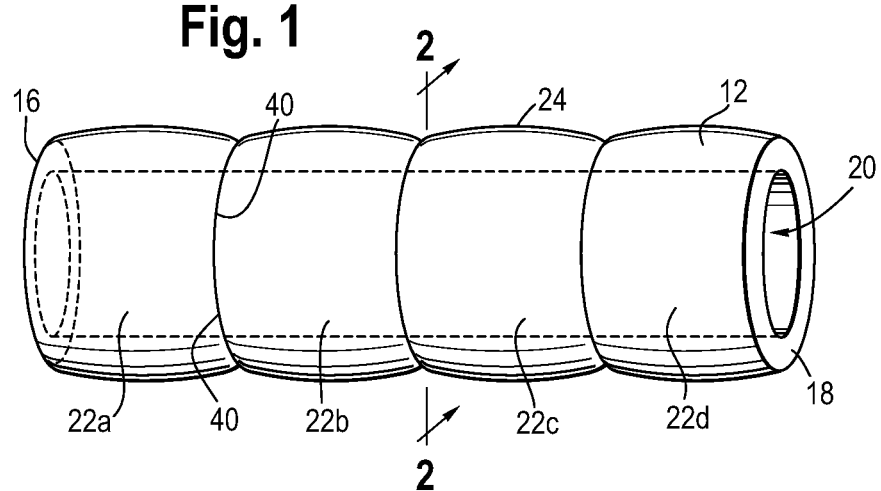
FIG. 1 depicts an embodiment of a graft during diastole.

FIG. 1 depicts an embodiment of a graft 8 during diastole where the pressure of blood in the lumen of graft is applying little or no pressure to the interior of the graft.

In one example, the graft 8 shown in FIGS. 1-4 may be sutured into a blood vessel. Although the graft 8 can be independent as represented in FIGS. 1-4, the graft 8 as described below may also be incorporated into new or existing vascular grafts, including stent-grafts, covered stents, arterial bypass grafts, and arterio-venous grafts.

The graft 8 may comprise a tubular body 12 of biocompatible graft material 14 having a proximal end 16 and a distal end 18 and a main lumen 20 extending therethrough. In an embodiment, the graft 8 has one or more compliance chambers 22 within a wall 24 of the tubular body 12 configured to match compliance of an adjacent vessel, duct, or lumen. The compliance chamber(s) 22 may be comprised of a cylindrical balloon or inflatable cylindrical lumen with an open channel. The open channel may contain the main lumen 20 that extends through the graft 8. Ridges 40 may be formed in between the compliance chambers 22.

The chambers may be construed using any known technique. In one example, two or more layers of graft material 14 may be adhered together to form chambers. For example, two tubes of graft material may be concentrically adhered to each other. In another example, the layers of graft material may be heat-set to form chambers. In another example, a balloon may be bonded between the layers of graft material 14.

In one example (shown in FIG. 1), four compliance chambers 22a, 22b, 22c, and 22d are incorporated into the tubular body 12 of the graft 8 and extend axially along the length of the tubular body. The compliance chambers 22 may be enclosed within a wall 24 of the graft material 14. For example, the compliance chambers 22 may be encapsulated or incorporated between sheets of graft material 14 that make up the wall 24 of the tubular body 12. There may be an internal side wall 42 and an external side wall 44.

The compliance chambers 22 may be made of the same biocompatible material as the graft material 14 (described in greater detail below), or the chambers 22 may be made of any other biocompatible material. In one example the compliance chambers 22 are made out of nylon or polyester.

Compliance chambers 22 may be at least partially filled with any suitable fluid, including a gel, gas, liquid, or vapor. For example, suitable gas may include carbon dioxide. Suitable vapors may include ethyl alcohol or dimethyl ether. Suitable liquids might include saline. The amount of gel, gas, liquid, or vapor may be predetermined.

Compliance chambers 22 may be inflated or filled to a particular volume or a particular pressure. In one example, the compliance chambers 22 are filled after the graft 8 has been delivered to the target site. In one example, they are filled using one or more ports (not shown) in each chamber during a filling state or step. The filling state or step may be before the graft 10 has been delivered to the target site.

The compressibility of each compliance chambers 22 can be adjusted by selection of dimensions, manufacturing materials, volume of gel and/or gas and/or vapor and/or liquid inside the chamber, and/or choice of gel, gas, vapor, or liquid within the chamber in order to create the desired compliance. For example, the volume and mixture of the gel, gas, liquid, or vapor selected to at least partially fill the compliance chambers 22 may be chosen so that one or more of the compliance chambers 22 is be compressed during systole because of the increased blood pressure, resulting in an increase in the compliance of the device compared to a standard graft.

As described in greater detail below, the configuration of these compliance chambers 22 can be altered along the length of the graft 8 to tailor the compliance of different regions of the graft 8 to the adjacent vessel. In other words, compliance chambers 22a, 22b, 22c, and 22d may each have different configurations of volume and mixture of gel, gas, liquid, or vapor to tailor the compliance chamber to an adjacent vessel.

The graft 8 and compliance chambers 22 may be any suitable selected diameter and may be constructed of any biocompatible graft material 14. The graft material 14 may be synthetic and/or naturally-derived material. Synthetic biocompatible polymers may include but are not limited to polyethylene terephthalate, polyurethane, nylon, polyester, high molecular weight polyethylene (such as Thoralon), polytetrafluoroethylene, or combinations thereof. The graft material 14 can be porous or non-porous and also may be impregnated or coated with one or more therapeutic substances. In one example, the graft material 14 may be constructed of the commercially available material referred to as PET, nylon, ePTFE, or Dacron. When used endoluminally, the graft material 14 should have sufficient flexibility to allow for navigation of the vasculature and delivery to a targeted area in the body. Preferably, the graft material 14 is a low profile material or an ultralow profile material.

The graft 8 may be any length, width, and diameter. Similarly, the compliance chambers 22 may be any length, width, and diameter. In one example, the graft 8 is between 4 mm and 8 mm in internal diameter, and is between 10 cm and 50 cm in length. In another example, the graft 8 is between 2 mm and 24 mm in internal diameter and between 10 cm to 100 cm in length. In one example, the compliance chambers 22 are between 3 cm and 25 cm in length, and are between 0.35 mm and 2 mm in wall thickness. For example, a graft having a 6 mm inner diameter and a 2 mm wall thickness would have an outer diameter of 10 mm. The compliance chambers 22 may be of uniform size or may vary along the length of the graft 8, and may have a compliance between 1% and 50%. The compliance chambers 22 may have a compliance of 3% to 30%.

The graft 8 may be delivered using any known delivery method, including minimally invasive techniques. In one example, the graft 8 can be inserted using a minimally invasive technique such as through a delivery catheter. For venous-arterial grafts, graft 8 could also be sewn in a vessel during an open procedure. Any known anchoring means may be provided with the graft 8 to prevent migration of the graft 8 in a vessel, duct, or lumen. In one example, a stent with one or more anchoring barbs may be attached to graft 8.

Figure 2:
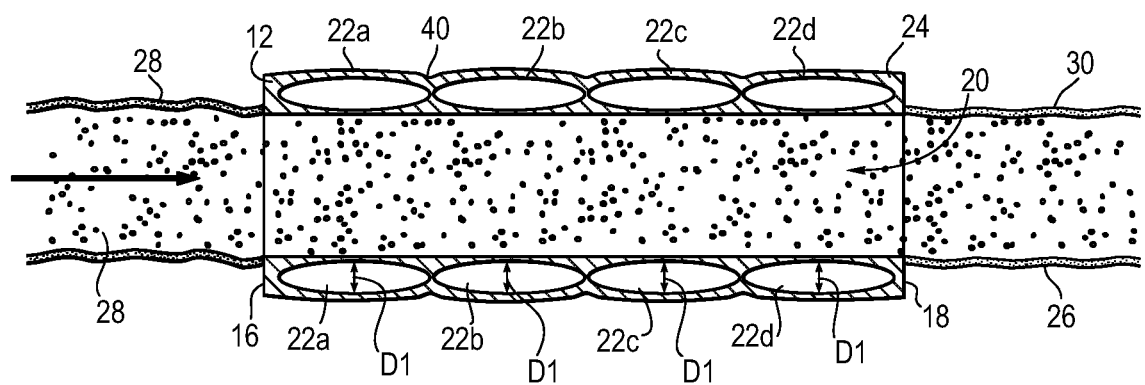
FIG. 2 depicts a cross-sectional view of the of the graft of FIG. 1 in a vessel during diastole.

FIG. 2 depicts a longitudinal cross-sectional view of the of the graft 8 of FIG. 1 in a vessel 26 during diastole. The vessel shown in FIG. 2 has an artery portion 28 and a vein portion 30, with a graft 8 in between. The graft 8 may be sewn into the vessel using any known technique. As shown in FIG. 2, graft 8 has a first or proximal end 16, a second or distal end 18, tubular body 12 having a wall 24 and a main lumen 20. The diameter and cross-sectional shape of the graft 8 allows for blood 28 to flow in a proximal to distal direction for example from an artery to a vein.

Compliance chambers 22a, 22b, 22c, and 22d are embedded within the wall 24 of the graft 8. As described above, the compliance chambers 22a, 22b, 22c, and 22d may be filled with different configurations of volume and mixture of fluid such as gel, gas, liquid, or vapor so that they are tailored to match compliance in an adjacent vessel, duct, or lumen. In one example, the compliance chambers 22a and 22b near the arterial end 32 of the graft are filled to have less compliance than those compliance chambers 22c and 22d nearer the venous end 34 of the graft. In other words, under systolic pressure, the chambers that are less compliant may compress very little or not at all as compared to those at the other end of the graft.

As shown in the example shown in FIG. 2, compliance chambers 22 may be configured to maintain their internal diameter (D1) during diastole (and, as shown below in FIGS. 3-4, the compliance chambers 22 may be compressed during systole thereby increasing the internal diameter due to the more compliant chambers being compressed).

Figure 3:
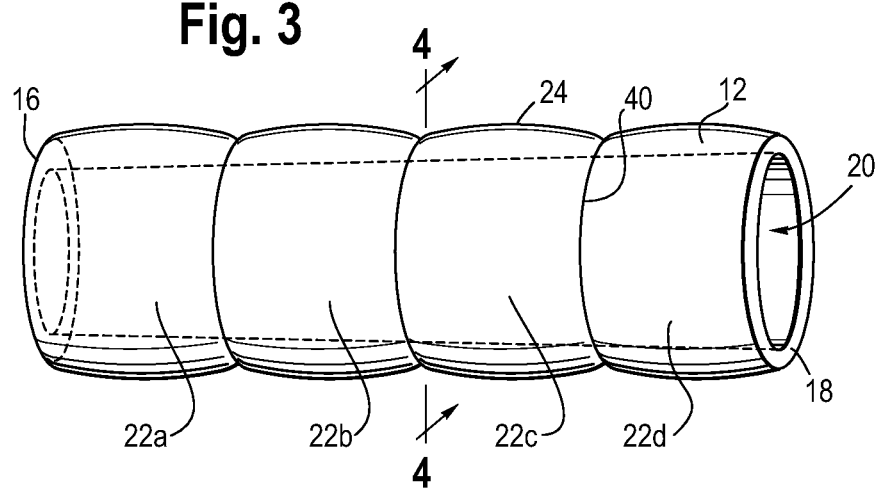
FIG. 3 depicts the graft of FIG. 1 during systole.

FIG. 3 depicts the graft of FIG. 1 during systole. During systole, there is higher pressure in the vessel, such as an aorta or artery, and hence higher pressure on the walls of the graft internally. The arterial end of the graft is substantially noncompliant, meaning that during systole it may not compress substantially (e.g., it may compress by an amount substantially similar to the compression of artery portion 28). It may be that the arterial end does not change from diastole to systole (or not change substantially). The compliance chambers 22 on the graft 8 allow the graft 8 to match the adjacent vessel during systole. For example, the compliance chambers 22 may be maintained during diastole but some would be compressed during systole because of the higher pressure in the vessel. Each compliance chamber may be compressed to different degrees (e.g., chamber 22a may compress insubstantially whereas chambers 22b, 22c, and 22d compress by increasing amounts, respectively).

As described above, compliance chambers 22a, 22b, 22c, and 22d may be filled with different configurations of volume and mixture of gel, gas, liquid, or vapor so that they are tailored to an adjacent vessel. In one example, the compliance chambers 22a and 22b near the arterial end 32 of the graft are filled to have less compliance than those compliance chambers 22c and 22d nearer the venous end 34 of the graft. In one example, the compliance in chamber 22d is greater than chamber 22c, which is greater than chamber 22b, which is greater than chamber 22a. In another example, the compliance in chamber 22d is greater than chambers 22c and 22b (which may be the same), which is greater than chamber 22a.

As shown in the example shown in FIG. 3, compliance chambers 22 may be compressed during systole.

Figure 4:
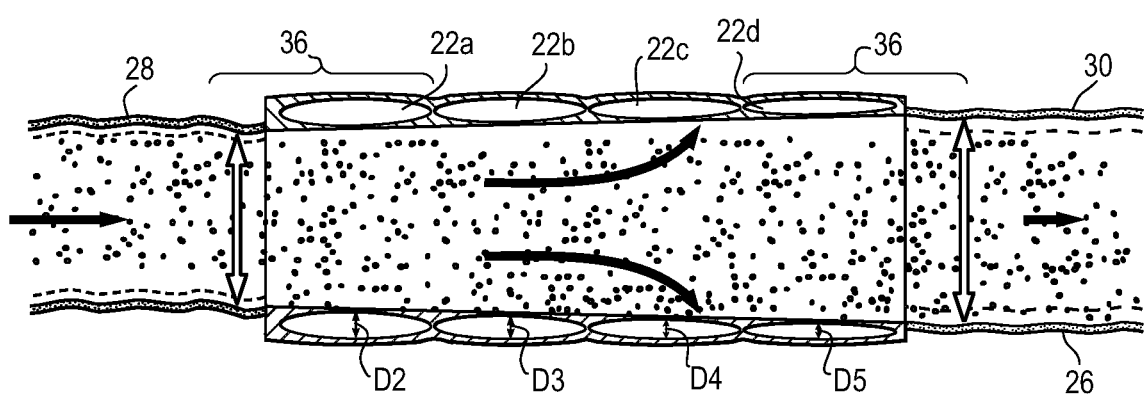
FIG. 4 depicts a cross-sectional view of the of the graft of FIG. 3 in a vessel during systole.

FIG. 4 depicts a cross-sectional view of the of the graft of FIG. 3 in a vessel during systole. (Note: the dashed lines show the vessel walls during lower pressure diastole).

During systole, the compliance of the arterial end 32 and venous end 34 of the graft 8 are matched to the compliance of the biological artery 28 and vein 30 to reduce mechanical stress on the vessels. As discussed above, compliance chamber 22a may be matched with the compliance of artery 28 at matched artery compliance zone 36. Compliance chamber 22d may be matched with the compliance of vein 30 at matched vein compliance zone 38.

As shown in FIG. 4, the compliance chamber near the artery 28 may compress less than those nearer the vein 30, resulting in a gradient of compliance along the length of the graft 8. In one example, there is a tubular body having a first end configured for attachment to a first vessel having a first compliance and second end configured for attachment to a second vessel having a second compliance different from the first compliance, the tubular body having an outer sidewall and an inner sidewall; a lumen extending between the first end and the second end; a first compressible chamber adjacent the first end of the tubular body and disposed between the inner side wall and the outer side wall; and a second compressible chamber adjacent the second end of the tubular and disposed between the inner side wall and the outer side wall; wherein the first chamber adjacent the first end of the tubular body is less compressible than the second chamber adjacent the second end of the tubular body such that first end of the tubular body substantially matches the first compliance and the second end of the tubular body substantially matches the second compliance. In one example, the compliance of the graft increases from the first end to the second end. In one example, the first end has a compliance configured to substantially match the compliance of the artery and the second end has a compliance configured to substantially match the compliance of the vein. In other words, the compliance gradient goes from the arterial end, i.e. less compliant to the venous end, more compliant.

Although the graft 8 shown in FIGS. 2 and 4 appear to be venous-arterial grafts where one end of the graft 8 is in the artery 28 and one end is in the vein 30, the graft 8 may be placed anywhere in the body. In one example, the graft 8 may be side to side such that one side of the graft 8 is near the artery 28 and one end is near the vein 30.

The graft disclosed above allows for the compliance of each end of the device to be designed to approximate that of the adjacent vessel, with the anticipation that this will result in reduced stenosis, improving graft function, hemodynamics, and patency rates.

An independent claim may read: A substantially tubular graft for placement between an artery and a vein and comprising:

a first end, a second end and a length in between the first end and the second end;

a compliance gradient from the first end to the second end, wherein the compliance of the graft increases substantially continuously from the first end to the second end; and wherein the first end has a compliance configured to substantially match the compliance of the artery and the second end has a compliance configured to substantially match the compliance of the vein.

A dependent claim may read: The substantially tubular graft of the above claim, further comprising a series of fluid filled chambers from the first end to the second end, wherein the compliances of the chambers increase from the first end to the second end.

While preferred embodiments of the invention have been described, it should be understood that the invention is not so limited, and modifications may be made without departing from the invention. Moreover, the advantages described herein are not necessarily the only advantages of the invention and it is not necessarily expected that every embodiment of the invention will achieve all of the advantages described.

We claim:

1. A graft for improving vascular compliance, the graft comprising:
a tubular body having a first end configured for attachment to an artery having a first compliance and second end configured for attachment to a vein having a second compliance different from the first compliance, the tubular body having an outer sidewall and an inner sidewall;
a lumen extending between the first end and the second end;
a first compressible chamber adjacent the first end of the tubular body and disposed between the inner side wall and the outer side wall; and
a second compressible chamber adjacent the second end of the tubular and disposed between the inner side wall and the outer side wall;
wherein the first chamber adjacent the first end of the tubular body is less compressible than the second chamber adjacent the second end of the tubular body such that first end of the tubular body substantially matches the first compliance and the second end of the tubular body substantially matches the second compliance.

2. The graft of claim 1, wherein at least a portion of each of the chambers is filled with a gel, gas, liquid, or vapor.

3. The graft of claim 1, further including at least one additional compressible chamber having a volume and disposed between the first and second compressible chambers, wherein the at least one additional compressible chamber is more compressible than the first compressible chamber and less compressible than the second compressible chamber, such that a compliance gradient is formed from the first end of the tubular body to the second end of the tubular body.

4. The graft of claim 2, wherein the first chamber is filled with a predetermined amount of a liquid, gas or vapor and the second chamber is filled with a different predetermined amount of at least one of a gel, gas, liquid, or vapor so that the first chamber and second chamber have different compliances.

5. The graft of claim 3, wherein each of the compressible chambers is filled with a different predetermined amount of a gel, liquid, gas or vapor different such that each of the compressible chambers has a different compliance.

6. The graft of claim 1 wherein the first chamber is configured for placement adjacent to an artery and the second chamber is configured for placement adjacent to a vein.

7. The graft of claim 1, wherein the tubular body comprises a third compressible chamber axially adjacent to the first compressible chamber and a fourth compressible chamber axially adjacent the second compressible chamber, wherein the third compressible chamber is more compressible than the first compressible chamber and the fourth compressible chamber is more compressible than the third compressible chamber and less compressible than the second compressible chamber, such that a compliance gradient is formed from the first end of the tubular body to the second end of the tubular body.

8. The graft of claim 7, wherein each of the first, second, third and fourth compressible chambers has a different predetermined amount of gel, gas, liquid, or vapor.

9. A substantially tubular graft for placement between an artery and a vein and comprising:
a first end, a second end, an internal side wall and an external side wall, and a length in between the first end and the second end,
a plurality of axial chambers disposed along the length of the graft between the first end and the second end; and
a compliance gradient from the first end to the second end, wherein the compliance of the graft increases from the first end to the second end; and
wherein the first end has a compliance configured to substantially match the compliance of the artery and the second end has a compliance configured to substantially match the compliance of the vein.

10. The graft of claim 9, wherein the plurality of chambers comprises a first chamber, a second chamber, a third chamber, and a fourth chamber,
wherein the first chamber is adjacent the first end and the fourth chamber is adjacent the second end, and the first and fourth chambers each contain a different predetermined amount of gel, gas, liquid, or vapor such that that the first chamber is less compliant than the fourth chamber.

11. The graft of claim 10, wherein the second and third chambers contain a different amount of gel, gas, liquid, or vapor from the first chamber such that each of the second and third chambers are more compliant than the first chamber.

12. The graft of claim 11, wherein the second and third chambers contain a different amount of gel, gas, liquid, or vapor from the fourth chamber such that each of the second and third chambers are less compliant than the fourth chamber.

13. The graft of claim 12, wherein the second chamber is more compliant than the first chamber and less compliant than the fourth chamber.

14. The graft of claim 10 wherein the second and third chambers have the same compliance.

15. A graft configured for placement between an artery and a vein comprising:
a first end configured to be attached to an artery;
a second end configured to be attached to a vein;
a lumen between the first end and the second end;
an internal side wall of graft material extending from the first end to the second end;
an external side wall of graft material extending from the first end to the second end and concentric with the internal side wall; and
an axial series of chambers between the internal side wall and the external side wall, each of the axial series of chambers extending circumferentially about a circumference of the graft;
wherein the first end of the graft has a compliance configured to match the compliance of the artery, and the second end of the graft has a compliance greater than the first end that is configured to match the compliance of the vein.

16. The graft of claim 15, wherein each chamber is configured to receive a predetermined amount of fluid, and wherein a chamber at the first end of The graft is less compliant than a chamber at the second end of The graft.

17. The graft of claim 16, wherein the axial series of chambers comprises four chambers extending from the first end to the second end, and wherein the compliance of the chambers increases from the first end to the second end such that a compliance gradient is formed from the first end to the second end.

18. The graft of claim 16, where each chamber has a compliance different from each other chamber such that compliance gradient from least compliant to most compliant is formed from the first end of the graft to the second end of the graft.

* * * * *